United States Patent
Zhang et al.

(10) Patent No.: US 11,591,374 B2
(45) Date of Patent: Feb. 28, 2023

(54) RECOMBINANT ESCHERICHIA COLI AND APPLICATION THEREOF IN SCREENING ERYTHRITOL-PRODUCING STRAINS

(71) Applicant: Jiangnan University, Wuxi (CN)

(72) Inventors: Juan Zhang, Wuxi (CN); Xueliang Qiu, Wuxi (CN); Jianghua Li, Wuxi (CN); Guocheng Du, Wuxi (CN); Jian Chen, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 443 days.

(21) Appl. No.: 16/916,266

(22) Filed: Jun. 30, 2020

(65) Prior Publication Data
US 2020/0325185 A1    Oct. 15, 2020

(30) Foreign Application Priority Data
Nov. 7, 2019  (CN) .......................... 201911081728.0

(51) Int. Cl.
*C07K 14/245* (2006.01)
*C12P 7/18* (2006.01)
*C12Q 1/02* (2006.01)

(52) U.S. Cl.
CPC .............. *C07K 14/245* (2013.01); *C12P 7/18* (2013.01); *C12Q 1/02* (2013.01)

(58) Field of Classification Search
CPC .............................. C07K 14/245; C12N 15/70
See application file for complete search history.

(56) References Cited

PUBLICATIONS

Lillo et al. "Functional Expression and Characterization of EryA, the Erythritol Kinase of Brucella Abortus, and Enzymatic Synthesis of L-Erythritol-4-phosphate" Bioorganic & Medicinal Chemistry Letters 13 (2003) 737-739 (Year: 2003).*
Sangri et al. "The genes for erythritol catabolism are organized as an inducible operon in Brucella abortus" Microbiology (2000), 146, 487-495 (Year: 2000).*

* cited by examiner

*Primary Examiner* — Thane Underdahl
(74) *Attorney, Agent, or Firm* — IPro, PLLC

(57) ABSTRACT

The present disclosure discloses recombinant *Escherichia coli* and application thereof in screening erythritol-producing strains, and belongs to the technical field of microorganisms. The recombinant *Escherichia coli* used in a method for screening an erythritol-producing strain disclosed by the present disclosure can well perform positive correlation induction on erythritol with different concentrations, so that the method for screening the erythritol-producing strain has the advantage of high sensitivity. High-concentration glucose is usually adopted as a fermentation substrate when erythritol is produced in a fermentation mode in the industry, but the method for screening the erythritol-producing strain disclosed by the present disclosure can overcome the interference of the high-concentration glucose, and under the interference of the high-concentration glucose, the recombinant *Escherichia coli* used in the method for screening the erythritol-producing strain can still well perform positive correlation induction on erythritol with different concentrations, and the correlation is higher than that without the interference of the glucose. Therefore, the method for screening the erythritol-producing strain has the advantage of strong anti-interference capability.

10 Claims, 5 Drawing Sheets

Specification includes a Sequence Listing.

```
                          SEQUENCE LISTING

<160> NUMBER OF SEQ ID NOS: 5

<210> SEQ ID NO 1
<211> LENGTH: 951
<212> TYPE: DNA
<213> ORGANISM: Artificial Sequence
<220> FEATURE:
<223> OTHER INFORMATION: Synthetic DNA

<400> SEQUENCE: 1
atggcagatg cagacgattc tctggcgctt cgcgccgcct ggcttcattt cgtcgccggc      60
atgactcagt ctgccgttgc caagcgcctt ggcctgcctt cggtgaaagc gcatcgtctc     120
atcgccaagg ccgttgccga cggcgcggtg aaagtgacca tcgacggtga catcaccgaa     180
tgcatcgatc tggaaaaccg tctggccgat ctttacggcc tcgattattg cgaggtcgca     240
cccgatattg gcgaggaagg cctgccgctg atggcgcttg gccatgcggg cgcgaatttc     300
atgcgccgcg aaatcgaaca tggcgatcat gaggtcatcg gcatcggcca tggccgcaca     360
ctttcggcag cggttggtta tatgccgcgt gtcatggcca atgatctgcg tttcgtctcg     420
cttctgggcg gcctcacgcg caattttgcc gccaacccgc atgacgtgat gcaccgcatc     480
gcggaaaaaa ccggaatgcc cgcttatgtg atgccggtgc ccttcttcgc caatacggcg     540
gaagaccgcg aagtgctgct ggcccaacgc ggtgtcacca cggttttcga catgggttgc     600
```

```
cgtgcggaac tgaagatcgt cggcattgga acggtcgatg cgcaggcgca gcttgtcaca    660
tccggcatga tagaacttgg cgaagtggaa gagatcgcca acctcggcgg cgtcggcgaa    720
atgctcggcc atttcttcaa tgccaatggc caatggctgg aaaccgcgct gacgggccgc    780
accatcgcgg cttccgtgga aaacgccgat atgagccgta tcgtggcgct tgcaggcggt    840
ctttccaagg tggacgccat tcgcgccgtg ctgaaaagcg ggcgtcttta cggcctcatc    900
accgacgaac ggacagcaaa ggcccttatc ggccagccga atggaaaatg a             951
```

<210> SEQ ID NO 2
<211> LENGTH: 717
<212> TYPE: DNA
<213> ORGANISM: Artificial Sequence
<220> FEATURE:
<223> OTHER INFORMATION: Synthetic DNA

<400> SEQUENCE: 2

```
atgggtaagg gagaagaact tttcactgga gttgtcccaa ttcttgttga attagatggt     60
gatgttaatg ggcacaaatt ttctgtcagt ggagagggtg aaggtgatgc aacatacgga    120
aaacttaccc ttaaatttat ttgcactact ggaaagctgc ctgttccttg gccaacactt    180
gtcactactc ttacttatgg tgttcaatgc ttttcaagat acccagatca tatgaagcgg    240
cacgacttct tcaagagcgc catgcctgag ggatacgtgc aggagaggac catcttcttc    300
aaggacgacg ggaactacaa gacacgtgct gaagtcaagt ttgagggaga cacctcgtc     360 aacagaatcg agcttaaggg aatcgatttc aaggaggacg gaaacatcct cggccacaag    420
ttggaataca actacaactc ccacaacgta tacatcatgg cagacaaaca aaagaatgga    480
atcaaagtta acttcaaaat tagacacaac attgaagatg gaagcgttca actagcagac    540
cattatcaac aaaatactcc aattggcgat ggccctgtcc ttttaccaga caaccattac    600
ctgtccacac aatctgccct ttcgaaagat cccaacgaaa agagagacca catggtcctt    660
cttgagtttg taacagctgc tgggattaca catggcatgg atgaactgta caaataa       717
```

<210> SEQ ID NO 3
<211> LENGTH: 742
<212> TYPE: DNA
<213> ORGANISM: Artificial Sequence
<220> FEATURE:
<223> OTHER INFORMATION: Synthetic DNA

<400> SEQUENCE: 3

```
tatcaaacgc cttcagcaat cctgccggtt gtcgttatgg aaacggatga tgcggcccgg     60
ctcaaaccgc tgacggtga tcgtccgcaa gcggaacgct caatttctat atcgcccaat    120
atggccagtt atcgcataag cagatgaccc cgcataagcg gtgcaggccg tgacggacaa    180
gagcatgaca tcctccacac gttccagacc cgctcccccg gctcctgaaa ccagatgtgc    240
cgcaatcaga aacttatgat agcggcgtgt atcaactgc tgaaatgatg ttataaagcc     300
tgatagctgt caatccgatg ttttgaaaac cttcgtgatt tggcataaaa tcgggcagaa    360
ttcgcgctga gccatagcga aatccaccgc taaatatggc ttgcccttat gagcgggcgg    420 ccttcgccc gccttgcaac catcgggata acacaaaaat aaatctaata aatacaatat    480
attgataaag acccactcat atctcccggt tttatatcgg acacatgatg ccggttccct    540
ccccttttag acgtagggtt ttccaccaca ttcaccttat gttgaaaaaa atacgccttg    600
ttaaaaattt tacagacagt tcgccagcgt tatgttatct ccaacatgcg ccatcgcccg    660
```

```
atttcgccat ggaaggggct gcgagcgacc tgttttcagt cgcgggagga aatccggatg      720
tttatgaaag cctgtgtcag cc                                              742

<210> SEQ ID NO 4
<211> LENGTH: 200
<212> TYPE: DNA
<213> ORGANISM: Artificial Sequence
<220> FEATURE:
<223> OTHER INFORMATION: Synthetic DNA

<400> SEQUENCE: 4 cctttagac gtagggtttt ccaccacatt caccttatgt tgaaaaaaat acgccttgtt       60
aaaaatttta cagacagttc gccagcgtta tgttatctcc aacatgcgcc atcgcccgat     120
ttcgccatgg aagggctgc gagcgacctg ttttcagtcg cgggaggaaa tccggatgtt     180
tatgaaagcc tgtgtcagcc                                                200

<210> SEQ ID NO 5
<211> LENGTH: 104
<212> TYPE: DNA
<213> ORGANISM: Artificial Sequence
<220> FEATURE:
<223> OTHER INFORMATION: Synthetic DNA

<400> SEQUENCE: 5
ctccaacatg cgccatcgcc cgatttcgcc atggaagggg ctgcgagcga cctgttttca      60
gtcgcgggag gaaatccgga tgtttatgaa agcctgtgtc agcc                     104
```

RECOMBINANT *ESCHERICHIA COLI* AND APPLICATION THEREOF IN SCREENING ERYTHRITOL-PRODUCING STRAINS

TECHNICAL FIELD

The present disclosure relates to recombinant *Escherichia coli* and application thereof in screening erythritol-producing strains, and belongs to the technical field of microorganisms.

BACKGROUND

Erythritol is a sugar alcohol with the smallest relative molecular mass found in nature, which not only has all excellent functions of sugar alcohol products, such as caries prevention and suitability for diabetic patients, but also uniquely has the characteristics of extremely low calorie ($\leq 1.66$ kJ-g) and extremely high tolerance dose (without side effects). The erythritol has good food processing adaptability and physiological health-care function, and is widely used in the fields of food, medicine, cosmetics, chemical industry and the like as a novel functional health-care food raw material at present.

Bacterial species for producing the erythritol include fungi, bacteria and the like, and many of the bacterial species produce polyols such as xylitol, ethanol and glycerol in addition to the erythritol. At present, erythritol-producing strains for commercial use are mainly *Aureobasidium* sp. variant strains in Japan and *Candida magnoliae* in South Korea. In view of the important application value and huge market demand of the erythritol, it is still the foundation of all research and development work to seek erythritol-producing strains with excellent fermentation performance.

An existing method for screening erythritol-producing strains mainly includes the steps of firstly culturing strains to be screened, and then determining the content of erythritol in fermentation liquor by using high performance liquid chromatography (HPLC). The method needs complex sample processing, is long in detection period, is not suitable for rapid detection of erythritol fermentation liquor, and is difficult to realize high-throughput screening of the erythritol-producing strains. Therefore, there is an urgent need to find a more efficient method for screening the erythritol-producing strains so as to overcome the defects of the existing screening method.

SUMMARY

Technical Problems

The technical problem to be solved by the present disclosure is to provide a high-efficiency method for screening an erythritol-producing strain.

Technical Scheme

In order to solve the abovementioned problems, the present disclosure provides a recombinant plasmid, and the recombinant plasmid uses a pET-22b(+) plasmid as an expression vector to express a gene encoding a transcriptional regulation factor and a marker gene; and a nucleotide sequence of the gene encoding the transcriptional regulation factor is shown as SEQ ID No.1.

In one implementation of the present disclosure, the recombinant plasmid uses the pET-22b(+) plasmid as the expression vector to express the gene encoding the transcriptional regulation factor, the marker gene and a transcriptional regulation factor binding sequence; and the transcriptional regulation factor binding sequence is shown as SEQ ID No.5.

In one implementation of the present disclosure, the recombinant plasmid is obtained by inserting the marker gene into the downstream of a T7 promoter of the pET-22b(+) plasmid, replacing a nucleotide sequence of an Lac I gene on the pET-22b(+) plasmid with the nucleotide sequence of the gene encoding the transcriptional regulation factor and replacing a nucleotide sequence of an Lac O gene with the transcriptional regulation factor binding sequence.

In one implementation of the present disclosure, the marker gene is a gene encoding a fluorescent protein.

In one implementation of the present disclosure, a nucleotide sequence of the gene encoding the fluorescent protein is shown as SEQ ID No.2.

The present disclosure further provides recombinant *Escherichia coli* containing the abovementioned recombinant plasmid.

In one implementation of the present disclosure, the recombinant *Escherichia coli* uses *Escherichia coli* BL21 (DE3) as an expression host.

The present disclosure further provides a method for screening an erythritol-producing strain, and the method includes inoculating the recombinant *Escherichia coli* into a fermentation supernatant of strains to be screened for culture to obtain a culture solution, and confirming the erythritol-producing capacity of the strains to be screened according to an expression amount of a marker gene in the culture solution.

In one implementation of the present disclosure, a culture medium is a glucose-containing culture medium.

In one implementation of the present disclosure, a concentration of glucose in the culture medium is 10-300 g/L.

The present disclosure further provides application of the recombinant plasmid or the recombinant *Escherichia coli* or the method for screening the erythritol-producing strain in screening erythritol-producing strains.

Beneficial Effects (1) The present disclosure provides the recombinant plasmid capable of being used for screening the erythritol-producing strains, the recombinant plasmid contains the gene encoding the transcriptional regulation factor and the marker gene, after the recombinant plasmid is introduced into the *Escherichia coli* BL21 (DE3), the recombinant *Escherichia coli* capable of being used for screening the erythritol-producing strains can be obtained. When the recombinant *Escherichia coli* is inoculated into the fermentation supernatant of the strains to be screened for culture, if the strains to be screened can produce erythritol, the erythritol produced by the strains to be screened can release the inhibition of the transcriptional regulation factor eryD to the marker gene in the recombinant plasmid, so that the marker gene is expressible, and then the expression of the marker gene can be detected in the culture solution obtained by co-culture. At the moment, the erythritol-producing strains can be screened out only by detecting fermentation liquor obtained by co-culture through a microplate reader. Therefore, using the recombinant plasmid for screening the erythritol-producing strains has the advantages of being easy to operate, short in detection period and high in detection efficiency.

(2) The present disclosure provides the recombinant *Escherichia coli* capable of being used for screening the erythritol-producing strains. The recombinant *Escherichia coli* contains the recombinant plasmid capable of expressing the gene encoding the transcriptional regulation factor and the marker gene, when the recombinant *Escherichia coli* is inoculated into the fermentation supernatant of the strains to be screened for culture, if the strains to be screened can produce erythritol, the erythritol produced by the strains to be screened can release the inhibition of the transcriptional regulation factor eryD to the marker gene in the recombinant plasmid, so that the marker gene is expressible, and then the expression of the marker gene can be detected in the culture solution obtained by co-culture. At the moment, the erythritol-producing strains can be screened out only by detecting the fermentation liquor obtained by co-culture through a microplate reader. Therefore, using the recombinant *Escherichia coli* for screening the erythritol-producing strains has the advantages of being easy to operate, short in detection period and high in detection efficiency.

(3) The present disclosure provides the method for screening the erythritol-producing strain. According to the method, the recombinant *Escherichia coli* containing the recombinant plasmid capable of expressing the gene encoding the transcriptional regulation factor and the marker gene is inoculated into the fermentation supernatant of the strains to be screened for culture, if the strains to be screened can produce erythritol, the erythritol produced by the strains to be screened can release the inhibition of the transcriptional regulation factor eryD to the marker gene in the recombinant plasmid, so that the marker gene is expressible, and then the expression of the marker gene can be detected in the culture solution obtained by co-culture. At the moment, the erythritol-producing strains can be screened out only by detecting the fermentation liquor obtained by co-culture through a microplate reader. Therefore, using the method provided by the present disclosure for screening the erythritol-producing strain has the advantages of being easy to operate, short in detection period and high in detection efficiency, and if a porous microplate is used in the process of screening the erythritol-producing strains by the method, the high-throughput breeding of the erythritol-producing strains can also be realized.

(4) The recombinant *Escherichia coli* used in the method for screening the erythritol-producing strain can well perform positive correlation induction on erythritol with different concentrations, so that the method for screening the erythritol-producing strain has the advantage of high sensitivity.

(5) High-concentration glucose is usually adopted as a fermentation substrate when erythritol is produced in a fermentation mode in the industry, but the method for screening the erythritol-producing strain disclosed by the present disclosure can overcome the interference of the high-concentration glucose, and under the interference of the high-concentration glucose, the recombinant *Escherichia coli* used in the method for screening the erythritol-producing strain can still well perform positive correlation induction on erythritol with different concentrations, and the correlation is higher than that without the interference of the glucose. Therefore, the method for screening the erythritol-producing strain has the advantage of strong anti-interference capability.

(6) The result of detecting the expression amount of the marker gene in the fermentation liquor obtained by co-culture through using the method disclosed by the present disclosure has the consistent trend with the result of detecting the content of erythritol in the fermentation liquor obtained by co-culture through using the liquid chromatography, so that the method for screening the erythritol-producing strain has the advantage of high accuracy.

DETAILED DESCRIPTION

Figure 1:
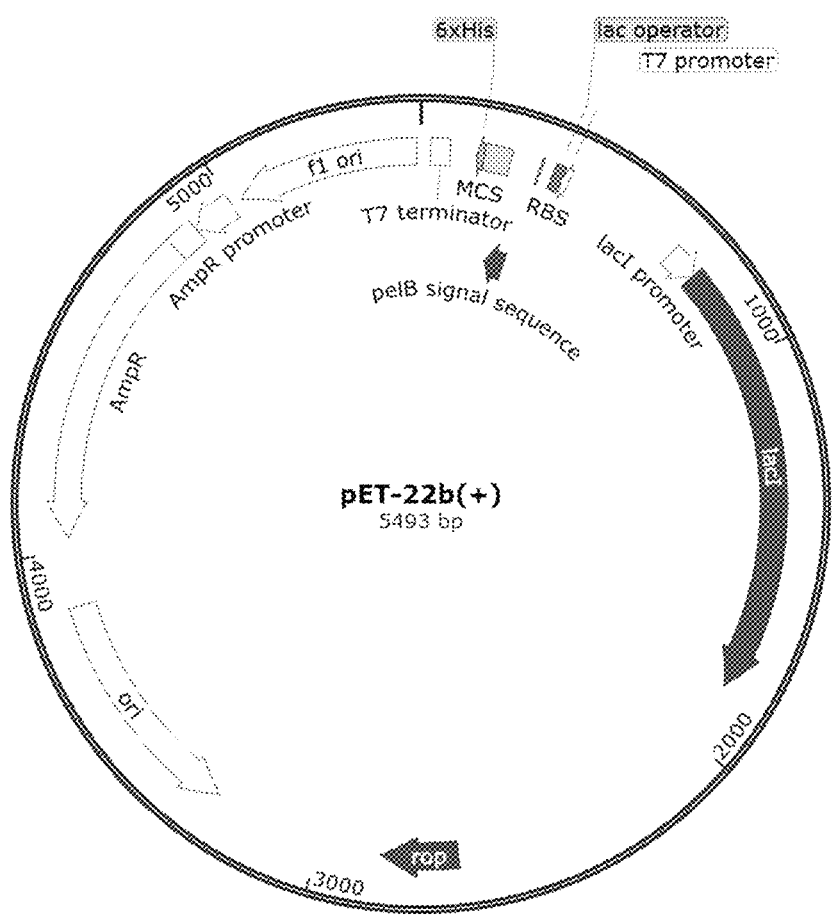
FIG. 1: a plasmid profile of a plasmid pET-22b(+).

*Escherichia coli* BL21 (DE3) involved in the following Examples is purchased from Sangon Bio-tech (Shanghai) Co., Ltd; and a pET-22b(+) plasmid involved in the following Examples is purchased from Nanjing Genscript Company.

Culture Media Involved in the Following Examples are as Follows:

LB liquid culture medium: sodium chloride 10 g/L, peptone 10 g/L, yeast powder 5 g/L, and ampicillin 100 ng/mL.

LB solid culture medium: sodium chloride 10 g/L, peptone 10 g/L, yeast powder 5 g/L, agar 20 g/L, and ampicillin 100 ng/mL.

YPD liquid culture medium: tryptone 20 g/L, yeast powder 10 g/L, and glucose 20 g/L.

YPD solid culture medium: tryptone 20 g/L, yeast powder 10 g/L, glucose 20 g/L, and agar 20 g/L.

A Detection Method Involved in the Following Examples is as Follows:

A method for detecting content of erythritol includes:

High performance liquid chromatography (1260 Infinity, Agilent, USA) is adopted to accurately determine erythritol and glucose in a supernatant of fermentation liquor. Mobile phase: dilute sulfuric acid (5 mm); column: an amine oRHPX-87H ion exclusion column; column temperature: 40° C.; flow rate: 0.6 mL/min; and detector: 1260RID.

Example 1: Recombinant Plasmid Capable of being Used for Screening Erythritol-Producing Strains A recombinant plasmid capable of being used for screening erythritol-producing strains is obtained by inserting a marker gene into the downstream of a T7 promoter of a pET-22b(+) plasmid, replacing a nucleotide sequence of an Lac I gene on the pET-22b(+) plasmid with a nucleotide sequence of a gene encoding a transcriptional regulation factor and replacing a nucleotide sequence of an Lac O gene with a transcriptional regulation factor binding sequence. The recombinant plasmid is named pET-22b(+)-eryD-3, wherein the nucleotide sequence of the gene encoding the transcriptional regulation factor is shown as SEQ ID No.1, and the transcriptional regulation factor binding sequence is shown as SEQ ID No.5. The recombinant plasmid pET-22b(+)-eryD-3 is prepared as follows.

Figure 3:
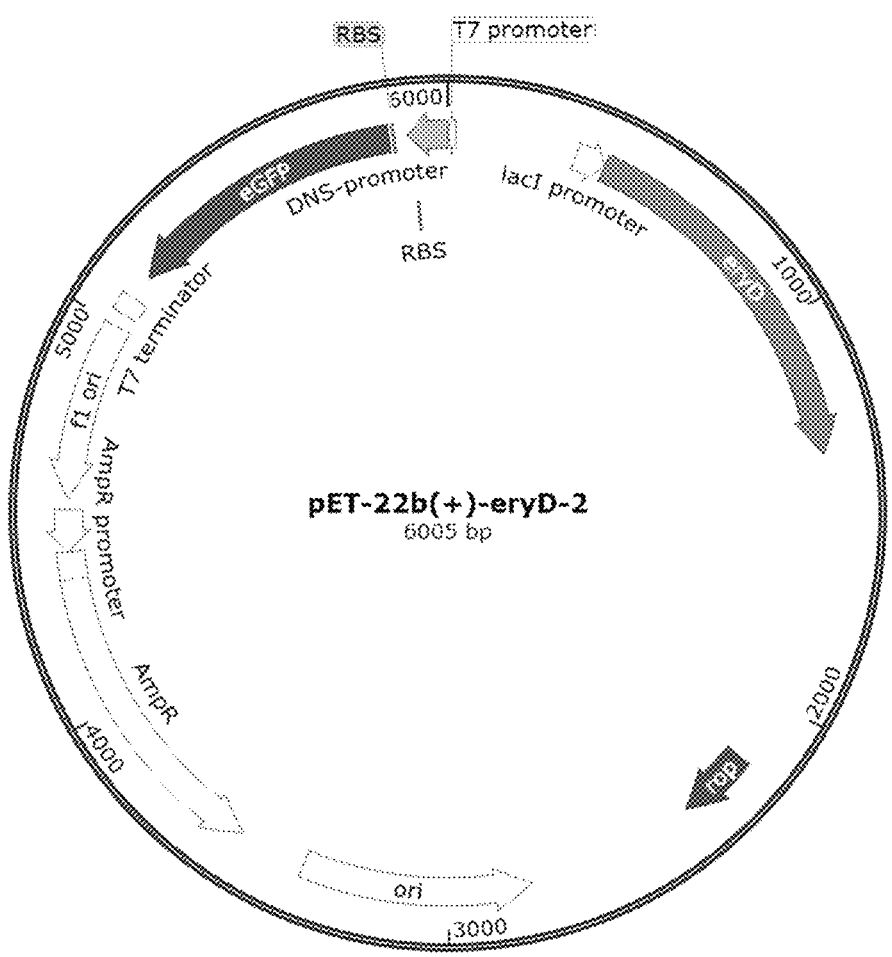
FIG. 3: a plasmid profile of a recombinant plasmid pET-22b(+)-eryD-2.

A 200 bp transcriptional regulation factor binding sequence at the upstream of an eryA initiation codon with a nucleotide sequence shown as SEQ ID No.4 is chemically synthesized (specifically see Table 1); the nucleotide sequence of the Lac O gene of the plasmid pET-22b(+) is replaced with the 200 bp transcriptional regulation factor binding sequence at the upstream of the eryA initiation codon by gene editing, the nucleotide sequence of the Lac I gene of the plasmid pET-22b(+) is replaced with the nucleotide sequence of the gene encoding the transcriptional regulation factor eryD by gene editing, and a gene encoding a fluorescent protein GFP is inserted into the downstream of a T7 promoter of the pET-22b(+) plasmid by gene editing so as to construct a recombinant plasmid pET-22b(+)-eryD-2 (a plasmid profile of the recombinant plasmid pET-22b(+)-eryD-2 is shown in FIG. 3); and on the basis of the recombinant plasmid pET-22b(+)-eryD-2, the 200 bp transcriptional regulation factor binding sequence at the upstream of the eryA initiation codon with the nucleotide sequence shown as SEQ ID No.4 is truncated by gene editing to a 104 bp transcriptional regulation factor binding sequence with a nucleotide sequence shown as SEQ ID No.5 (specifically see Table 1), so the recombinant plasmid pET-22b(+)-eryD-3 is obtained.

Example 2: Recombinant *Escherichia coli* Capable of being Used for Screening Erythritol-Producing Strains A recombinant *Escherichia coli* capable of being used for screening erythritol-producing strains is obtained by transforming the recombinant plasmid pET-22b(+)-eryD-3 capable of being used for screening the erythritol-producing strains described in Example 1 into *Escherichia coli*.

Example 3: Construction of Recombinant Plasmid and Recombinant *Escherichia coli* Capable of being Used for Screening Erythritol-Producing Strains The specific steps are as follows.

(1) Construction and First Verification of the Recombinant Plasmid and the Recombinant *Escherichia coli*

Figure 2:
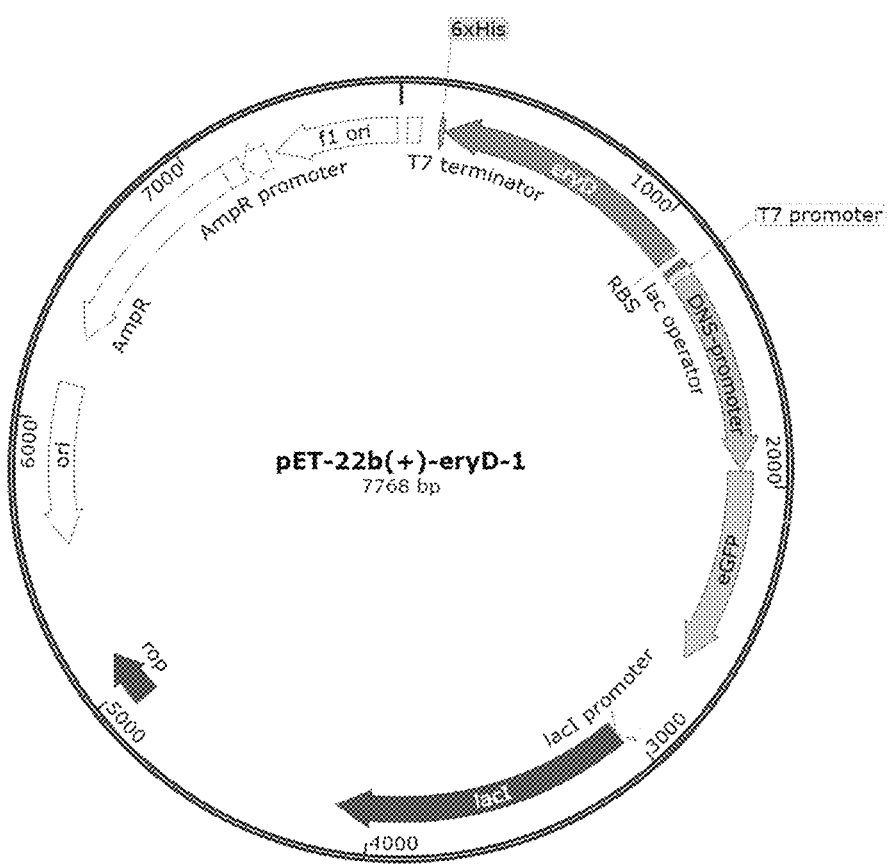
FIG. 2: a plasmid profile of a recombinant plasmid pET-22b(+)-eryD-1.

A gene encoding a transcriptional regulation factor eryD with a nucleotide sequence shown as SEQ ID No.1 (specifically see Table 1), a gene encoding a fluorescent protein GFP with a nucleotide sequence shown as SEQ ID No.2 (specifically see Table 1) and a promoter on the upstream of an eryA gene in ery Operon with a nucleotide sequence shown as SEQ ID No.3 (specifically see Table 1) are obtained through chemical synthesis; the gene encoding the transcriptional regulation factor eryD is inserted into the downstream of a T7 promoter of a pET-22b(+) plasmid by gene editing, the promoter on the upstream of the eryA gene in the ery Operon and the gene encoding the fluorescent protein GFP are inserted into the upstream of the T7 promoter of the pET-22b(+) plasmid by gene editing on the reverse side in sequence, and a recombinant plasmid pET-22b(+)-eryD-1 is obtained (a plasmid profile of the plasmid pET-22b(+) is shown in FIG. 1, and a plasmid profile of the recombinant plasmid pET-22b(+)-eryD-1 is shown in FIG. 2).

The obtained recombinant plasmid pET-22b(+)-eryD-1 is introduced into *E. coli* BL21 (DE3); the transformed *E. coli* BL21 (DE3) is streaked on an LB solid culture medium, and cultured for 10 h under the condition of 37° C.; positive transformants are picked and inoculated into an LB liquid culture medium, and cultured for 16 h under the condition of 37° C., thalli are collected, a genome is extracted and verified by PCR, and the recombinant *E. coli* BL21 (DE3)/pET-22b(+)-eryD-1 is obtained if it passes the verification.

The recombinant *E. coli* BL21 (DE3)/pET-22b(+)-eryD-1 is streaked on the LB solid culture medium and cultured for 10 h under the condition of 37° C.; a single colony is picked, inoculated into the LB liquid culture medium, and cultured for 10 h under the condition of 37° C.; seed liquid is inoculated into the LB liquid culture medium containing IPTG with the concentration of 0.5 mM at the inoculation amount of 10% (v/v), and cultured for 16 h under the condition of 37° C. to obtain fermentation liquor; and 200 µL of the fermentation liquor is taken, the fluorescence intensity in the fermentation liquor is measured by using a microplate reader, and the detection result is as follows: no fluorescence is observed in the fermentation liquor.

As can be seen, construction of the recombinant *E. coli* BL21 (DE3)/pET-22b(+)-eryD-1 fails, presumably due to two reasons: one is that the T7 promoter has leaky expression of the eryD, so that the ery Operon promoter is repressed, and the fluorescent protein is not expressed; and the other one is that the promoter cannot be successfully started in *E. coli* because an RBS sequence of the promoter is too far from an initiation codon of the gene encoding the fluorescent protein GFP or the RBS sequence of the promoter cannot play a role properly.

(2) First Transformation and Second Verification of the Recombinant Plasmid and the Recombinant *Escherichia coli*

In order to find out the reason why the construction of the recombinant *E. coli* BL21 (DE3)/pET-22b(+)-eryD-1 fails, the eryD gene is knocked out from the plasmid by gene editing on the basis of the recombinant *E. coli* BL21 (DE3)/pET-22b(+)-eryD-1, and the result shows that there is still no obvious fluorescent protein expression in the fermentation liquor. It can be seen that the reason why the construction of the recombinant *E. coli* BL21 (DE3)/pET-22b(+)-eryD-1 fails is not the leaky expression of the eryD by the T7 promoter.

In order to find out the reason why the construction of the recombinant *E. coli* BL21 (DE3)/pET-22b(+)-eryD-1 fails, on the basis of the recombinant *E. coli* BL21 (DE3)/pET-22b(+)-eryD-1, a 16 bp sequence on the upstream of the initiation codon of the gene encoding the fluorescent protein GFP is knocked out from the plasmid by circular PCR, and the result shows that there is still no obvious fluorescent protein expression in the fermentation liquor. It can be seen that the reason why the construction of the recombinant *E. coli* BL21 (DE3)/pET-22b(+)-eryD-1 fails is not that the promoter cannot be successfully started in the *Escherichia coli* due to the too long distance from the RBS sequence of the promoter to the initiation codon of the gene encoding the fluorescent protein GFP.

In order to find out the reason why the construction of the recombinant *E. coli* BL21 (DE3)/pET-22b(+)-eryD-1 fails, on the basis of the recombinant *E. coli* BL21 (DE3)/pET-22b(+)-eryD-1, the RBS sequence "AAGGAG" of the plasmid pET-22b(+) is inserted into the upstream of the initiation codon of the gene encoding the fluorescent protein GFP through circular PCR and is away from a translation start site ATG of the gene encoding the fluorescent protein GFP by eight base pairs, and the result shows that there is still no obvious fluorescent protein expression in the fermentation liquor. It can be seen that the reason why the construction of the recombinant *E. coli* BL21 (DE3)/pET-22b(+)-eryD-1 fails is not that the promoter cannot be successfully started in the *Escherichia coli* as the RBS sequence of the promoter cannot play a role properly.

Based on the above, the reason why the construction of the recombinant *E. coli* BL21 (DE3)/pET-22b(+)-eryD-1 fails is most likely that the promoter located on the upstream of the eryA gene in the ery Operon cannot be expressed alone in the *E. coli* BL21 (DE3) or the expression is too weak. Therefore, a 200 bp transcriptional regulation factor binding sequence at the upstream of the eryA initiation codon with a nucleotide sequence shown as SEQ ID No.4 is chemically synthesized (specifically see Table 1); a nucleotide sequence of an Lac O gene of the plasmid pET-22b(+) is replaced with the 200 bp transcriptional regulation factor binding sequence at the upstream of the eryA initiation codon by gene editing, a nucleotide sequence of an Lac I gene of the plasmid pET-22b(+) is replaced with the nucleotide sequence of the gene encoding the transcriptional regulation factor eryD by gene editing, and the gene encoding the fluorescent protein GFP is inserted into the downstream of the T7 promoter of the pET-22b(+) plasmid by gene editing so as to construct a new recombinant plasmid pET-22b(+)-eryD-2 (a plasmid profile of the recombinant plasmid pET-22b(+)-eryD-2 is shown in FIG. 3).

The obtained recombinant plasmid pET-22b(+)-eryD-2 is introduced into the *E. coli* BL21 (DE3); the transformed *E. coli* BL21 (DE3) is streaked on the LB solid culture medium, and cultured for 10 h under the condition of 37° C.; positive transformants are picked and inoculated into the LB liquid culture medium, and cultured for 16 h under the condition of 37° C., thalli are collected, a genome is extracted and verified by PCR, and the recombinant *E. coli* BL21 (DE3)/pET-22b(+)-eryD-2 is obtained if it passes the verification.

The recombinant *E. coli* BL21 (DE3)/pET-22b(+)-eryD-2 is streaked on the LB solid culture medium and cultured for 10 h under the condition of 37° C.; a single colony is picked, inoculated into the LB liquid culture medium, and cultured for 10 h under the condition of 37° C.; seed liquid is inoculated into the LB liquid culture medium containing IPTG with the concentration of 0.5 mM at the inoculation amount of 10% (v/v), and cultured for 16 h under the condition of 37° C. to obtain fermentation liquor; and 200 μL of the fermentation liquor is taken, the fluorescence intensity in the fermentation liquor is measured by using the microplate reader, and the detection result is as follows: there is no obvious fluorescent protein expression in the fermentation liquor. It can be seen that construction of the recombinant *E. coli* BL21 (DE3)/pET-22b(+)-eryD-2 still fails.

(3) Second Transformation and Third Verification of the Recombinant Plasmid and the Recombinant *Escherichia coli*

On the basis of the recombinant *E. coli* BL21 (DE3)/pET-22b(+)-eryD-2, the 200 bp transcriptional regulation factor binding sequence at the upstream of the eryA initiation codon with the nucleotide sequence shown as SEQ ID No.4 is truncated by gene editing to a 104 bp transcriptional regulation factor binding sequence with a nucleotide sequence shown as SEQ ID No.5 (specifically see Table 1), the result shows that there is no obvious fluorescent protein expression in the fermentation liquor, and the recombinant *Escherichia coli* is named recombinant *E. coli* BL21 (DE3)/pET-22b(+)-eryD-3.

The recombinant *E. coli* BL21 (DE3)/pET-22b(+)-eryD-3 is streaked on the LB solid culture medium, and cultured for 10 h under the condition of 37° C.; a single colony is picked, inoculated into the LB liquid culture medium, and cultured for 10 h under the condition of 37° C.; and seed liquid is inoculated into the LB liquid culture medium containing IPTG with the concentration of 0.5 mM at the inoculation amount of 10% (v/v), and cultured for 16 h under the condition of 37° C. to obtain fermentation liquor A.

The recombinant *E. coli* BL21 (DE3)/pET-22b(+)-eryD-3 is streaked on the LB solid culture medium, and cultured for 10 h under the condition of 37° C.; a single colony is picked, inoculated into the LB liquid culture medium, and cultured for 10 h under the condition of 37° C.; and seed liquid is inoculated into an LB liquid culture medium containing IPTG with the concentration of 0.5 mM and erythritol with the concentration of 100 mM at the inoculation amount of 10% (v/v), and cultured for 16 h under the condition of 37° C. to obtain fermentation liquor B.

Figure 4:
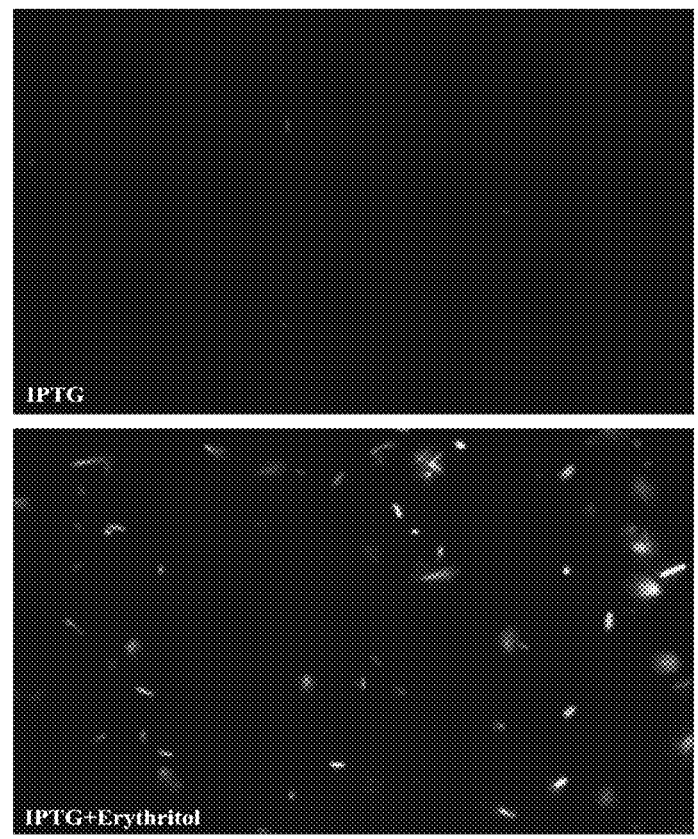
FIG. 4: influence of erythritol induction on fluorescence intensity in fermentation liquor obtained by fermenting recombinant *E. coli* BL21 (DE3)/pET-22b(+)-eryD-3.

10 μL of the fermentation liquor A and 10 μL of the fermentation liquor B are taken, the fluorescence intensities in the fermentation liquor A and the fermentation liquor B are measured by a fluorescence microscope respectively, and the detection result is shown in FIG. 4.

As can be seen from FIG. 4, the addition of the erythritol obviously increases the fluorescence intensity in the fermentation liquor obtained by fermenting the recombinant *E. coli* BL21 (DE3)/pET-22b(+)-eryD-3. It can be seen that the recombinant *E. coli* BL21 (DE3)/pET-22b(+)-eryD-3 can respond to the erythritol, and has potential for high-throughput detection of the erythritol.

(4) Fourth Verification of the Recombinant Plasmid and the Recombinant *Escherichia coli*

The recombinant *E. coli* BL21 (DE3)/pET-22b(+)-eryD-3 is streaked on the LB solid culture medium, and cultured for 10 h under the condition of 37° C.; a single colony is picked, inoculated into the LB liquid culture medium, and cultured for 10 h under the condition of 37° C.; and seed liquid is inoculated into LB culture media containing erythritol with the concentrations of 5 mmol/L, 10 mmol/L, 50 mmol/L, 100 mmol/L, 250 mmol/L, 500 mmol/L and 1000 mmol/L respectively at the inoculation amount of 10% (v/v), and cultured under the condition of 37° C. to obtain fermentation liquor.

Figure 5:
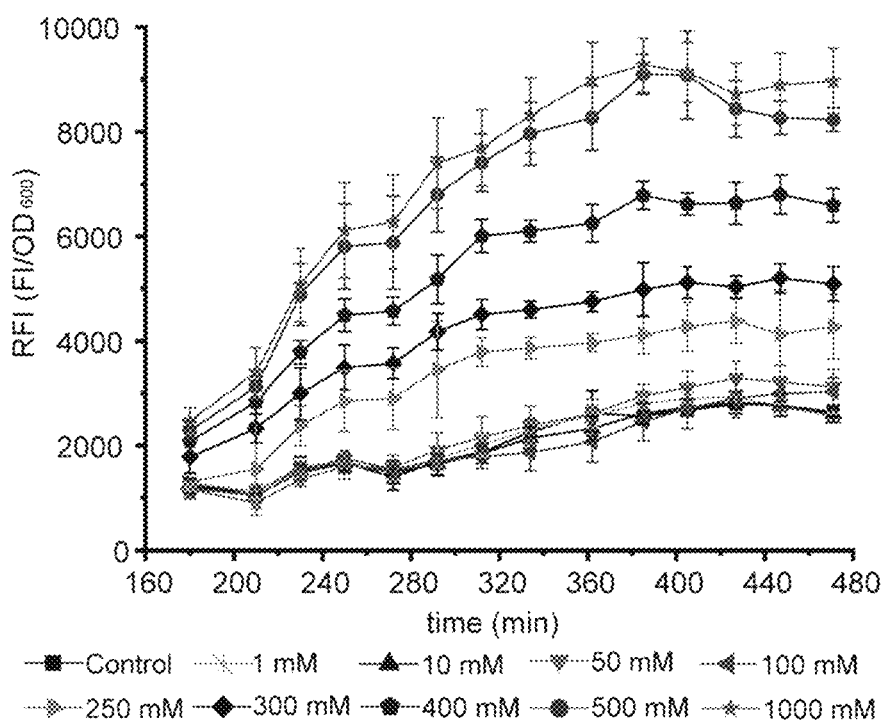
FIG. 5: influence of erythritol induction concentrations on fluorescence intensity in fermentation liquor obtained by fermenting recombinant *E. coli* BL21 (DE3)/pET-22b(+)-eryD-3.

The fluorescence intensities in the fermentation liquor are measured by the microplate reader every 20 min after 3 h of culture, and the detection result is shown in FIG. 5.

As can be seen from FIG. 5, the erythritol with the concentration below 250 mmol/L does not play a role in enhancing the expression of the fluorescent protein by the recombinant *E. coli* BL21 (DE3)/pET-22b(+)-eryD-3, but reduces the expression level of the fluorescent protein in the fermentation liquor; and the erythritol with the concentration between 250 mmol/L and 500 mmol/L significantly enhances the expression of the fluorescent protein by the recombinant *E. coli* BL2 (DE3)/pET-22b(+)-eryD-3, resulting in a significant increase in the expression level of the fluorescent protein in the fermentation liquor. It can be seen that the response range of the recombinant *E. coli* BL21 (DE3)/pET-22b(+)-eryD-3 to the erythritol is 250-500 mmol/L, and the sensitivity is high.

(5) Fifth Verification of the Recombinant Plasmid and the Recombinant *Escherichia coli*

The recombinant *E. coli* BL21 (DE3)/pET-22b(+)-eryD-3 is streaked on the LB solid culture medium, and cultured for 10 h under the condition of 37° C.; a single colony is picked, inoculated into the LB liquid culture medium, and cultured for 10 h under the condition of 37° C.; and seed liquid is inoculated into LB culture media containing glucose with the concentration of 100 g/L and erythritol with the concentrations of 5 mmol/L, 10 mmol/L, 50 mmol/L, 100 mmol/L, 250 mmol/L, 500 mmol/L and 1000 mmol/L respectively at the inoculation amount of 10% (v/v), and cultured under the condition of 37° C. to obtain fermentation liquor.

Figure 6:
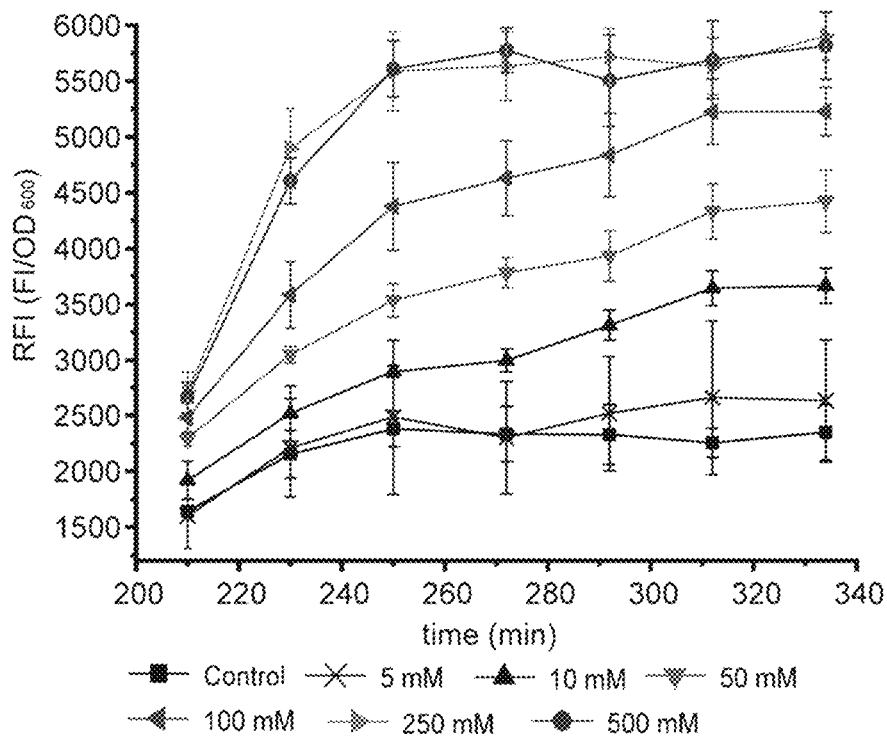
FIG. 6: influence of glucose concentrations on fluorescence intensity in fermentation liquor obtained by fermenting recombinant *E. coli* BL21 (DE3)/pET-22b(+)-eryD-3.

The fluorescence intensities in the fermentation liquor are measured by the microplate reader every 20 min after 3 h of culture, and the detection result is shown in FIG. 6.

As can be seen from FIG. 6, the response range of the recombinant E. coli BL21 (DE3)/pET-22b(+)-eryD-3 to the erythritol is changed to 10-250 mmol/L under the interference of the glucose with the concentration of 100 g/L, and the recombinant E. coli BL21 (DE3)/pET-22b(+)-eryD-3 well performs positive correlation induction on the erythritol with the experiment concentrations when being cultured for 250 min. It can be seen that the sensitivity of the recombinant E. coli BL21 (DE3)/pET-22b(+)-eryD-3 to the erythritol is improved and the anti-interference capability is strong after addition of the glucose.

Based on the above, the recombinant E. coli BL21 (DE3)/pET-22b(+)-eryD-3 can be responsive to the erythritol, has high sensitivity to erythritol concentrations, can overcome the interference of the high-concentration glucose, and has higher sensitivity to the erythritol under the interference of the high-concentration glucose, and thus the recombinant E. coli BL21 (DE3)/pET-22b(+)-eryD-3 can be used for screening the erythritol-producing strains.

Example 4: Application of Recombinant Escherichia coli Capable of being Used for Screening Erythritol-Producing Strains The specific steps are as follows.

Five strains of Yarrowia lipolytica which can produce erythritol are randomly selected. Because the fermentation production of the erythritol by the Yarrowia lipolytica requires high dissolved oxygen, 2 mL 96-well plates are adopted for fermentation culture, and the plates are sealed with sealing membranes and stainless steel covers respectively.

The extracted Yarrowia lipolytica capable of producing the erythritol is streaked on a YPD solid culture medium, and cultured for 40 h under the condition of 30° C. to obtain a single colony of the Yarrowia lipolytica; the single colony of the Yarrowia lipolytica is picked, inoculated into a YPD liquid culture medium, and cultured for 20 h under the condition of 30° C. to obtain seed liquid of the Yarrowia lipolytica; the seed liquid of the Yarrowia lipolytica is inoculated into a YPD liquid culture medium at the inoculation amount of 5% (v/v), glucose is supplemented into the YPD liquid culture medium until the concentration of the glucose in the YPD liquid culture medium is 150 g/L, and the seed liquid is cultured for 40-150 h under the condition of 30-35° C. to obtain fermentation liquor; the fermentation liquor is centrifuged to obtain a fermentation supernatant; the recombinant E. coli BL21 (DE3)/pET-22b(+)-eryD-3 obtained in Example 3 is streaked on an LB solid culture medium, and cultured for 10 h under the condition of 37° C. to obtain a single colony of the recombinant E. coli BL21 (DE3)/pET-22b(+)-eryD-3; the single colony of the recombinant E. coli BL21 (DE3)/pET-22b(+)-eryD-3 is picked, inoculated into an LB liquid culture medium, and cultured for 16 h under the condition of 37° C. to obtain seed liquid of the recombinant E. coli BL21 (DE3)/pET-22b(+)-eryD-3; and the seed liquid of the recombinant E. coli BL21 (DE3)/pET-22b(+)-eryD-3 is inoculated into the fermentation supernatant at the inoculation amount of 10%, 0.5 mM of IPTG and 100 ng/mL of ampicillin are added into the fermentation supernatant and cultured for 3 h under the condition of 37° C., after 3 h, the fluorescence intensity in a culture solution is measured by a microplate reader, and the content of the erythritol in the culture solution is measured by high performance liquid chromatography.

The fluorescence intensity measured by the microplate reader in the culture solution is consistent with the content change measured by the high performance liquid chromatography of the erythritol in the culture solution. This further demonstrates that the recombinant E. coli BL21 (DE3)/pET-22b(+)-eryD-3 can be used for screening the erythritol-producing strains.

TABLE 1

Nucleotide Sequence of Each Gene

| Gene | Nucleotide Sequence |
|---|---|
| Gene encoding transcriptional regulation factor eryD | SEQ ID No. 1:<br>atggcagatgcagacgattctctggcgcttcgcgccgcctggcttcatttcgtcgccggcatgactcag<br>tctgccgttgccaagcgccttggcctgccttcggtgaaagcgcatcgtctcatcgccaaggccgttgcc<br>gacggcgcggtgaaagtgaccatcgacggtgacatcaccgaatgcatcgatctggaaaaccgtctggcc<br>gatctttacggcctcgattattgcgaggtcgcacccgatattggcgaggaaggcctgccgctgatggcg<br>cttggccatgcgggcgcgaatttcatgcgccgcgaaatcgaacatggcgatcatgaggtcatcggcatc<br>ggccatggccgcacactttcggcagcggttggttatatgccgcgtgtcatggccaatgatctgcgtttc<br>gtctcgcttctgggcggcctcacgcgcaattttgccgccaacccgcatgacgtgatgcaccgcatcgcg<br>gaaaaaaccggaatgcccgcttatgtgatgccggtgcccttcttcgccaatacggcggaagaccgcgaa<br>gtgctgctggcccaacgcggtgtcaccacggttttcgacatgggttgccgtgcggaactgaagatcgtc<br>ggcattggaacggtcgatgcgcaggcgcagcttgtcacatccggcatgatagaacttggcgaagtggaa<br>gagatcgccaacctcggcggcgtcggcgaaatgctcggccatttcttcaatgccaatggccaatggctg<br>gaaaccgcgctgacgggccgcaccatcggcgcttccgtggaaaacgccgatatgagccgtatcgtggcg<br>cttgcaggcggtctttccaaggtggacgccattcgcgccgtgctgaaaagcgggcgtctttacggcctc<br>atcaccgacgaacggacagcaaaggcccttatcggccagccgaatggaaaataa |
| Gene encoding fluorescent protein GFP | SEQ ID No. 2:<br>atgggtaagggagaagaacttttcactggagttgtcccaattcttgttgaattagatggtgatgttaat<br>gggcacaaattttctgtcagtggagagggtgaaggtgatgcaacatacggaaaacttacccttaaattt<br>atttgcactactggaaagctGcctgttccttggccaacacttgtcactactcttacttatggtgttcaa<br>tgcttttcaagatacccagatcatatgaagcggcacgacttcttcaagagcgccatgcctgagggatac<br>gtgcaggagaggaccatcttcttcaaggacgacgggaactacaagacacgtgctgaagtcaagtttgag<br>ggagacaccctcgtcaacagaatcgagcttaagggaatcgatttcaaggaggacggaaacatcctcggc<br>cacaagttggaatacaactacaactcccacaacgtatacatcatggcagacaaacaaaagaatggaatc<br>aaagttaacttcaaaattagacacaacattgaagatggaagcgttcaactagcagaccattatcaacaa<br>aatactccaattggcgatggccctgtccttttaccagacaaccattacctgtccacacaatctgccctt |

TABLE 1-continued

Nucleotide Sequence of Each Gene

| Gene | Nucleotide Sequence |
|---|---|
| | tcgaaagatcccaacgaaaagagagaccacatggtccttcttgagtttgtaacagctgctgggattaca<br>catggcatggatgaactgtacaaataa |
| Promoter located on the upstream of eryA gene in ery Operon | SEQ ID No. 3:<br>tatcaaacgccttcagcaatcctgccggttgtcgttatggaaacggatgatgcggcccggctcaaaccg<br>cctgacggtgatcgtccgcaagcggaacgctcaatttctatatcgcccaatatggccagttatcgcata<br>agcagatgacccgcataagcggtgcaggccgtgacggacaagagcatgacatcctccacacgttccag<br>acccgctcccccggctcctgaaaccagatgtgccgcaatcagaaacttatgatagcggcgtgttatcaa<br>ctgctgaaatgatgttataaagcctgatagctgtcaatccgatgttttgaaaaccttcgtgatttggca<br>taaaatcgggcagaattcgcgctgagccatagcgaaatccaccgctaaatatggcttgcccttatgagc<br>gggcggcctttcgcccgccttgcaaccatcgggataacacaaaaataaatctaataaatacaatatatt<br>gataaagacccactcatatctcccggttttatatcggacacatgatgccggttccctcccctttttagac<br>gtagggttttccaccacattcaccttatgttgaaaaaaatacgccttgttaaaaattttacagacagtt<br>acgccagcgtttgttatctccaacatgcgccatcgcccgatttcgccatggaaggggctgcgagcgacc<br>tgttttcagtcgcgggaggaaatccggatgtttatgaaagcctgtgtcagcc |
| 200 bp transcriptional regulation factor binding sequence at the upstream of eryA initiation codon | SEQ ID No. 4:<br>ccttttagacgtagggttttccaccacattcaccttatgttgaaaaaaatacgccttgttaaaaattt<br>gacaacagttcgccagcgttatgttatctccaacatgcgccatcgcccgatttcgccatggaagggct<br>gcgagcgacctgttttcagtcgcgggaggaaatccggatgtttatgaaagcctgtgtcagcc |
| 104 bp transcriptional regulation factor binding sequence at the upstream of eryA initiation codon | SEQ ID No. 5:<br>ctccaacatgcgccatcgcccgatttcgccatggaaggggctgcgagcgacctgttttcagtcgcggga<br>ggaaatccggatgtttatgaaagcctgtgtcagcc |

Although the present disclosure has been disclosed above in terms of exemplary Examples, it is not intended to limit the present disclosure, and various changes and modifications may be made by those skilled in the art without departing from the spirit and scope of the present disclosure, so the protection scope of the present disclosure should be defined in the appended claims.

What is claimed is:

1. A recombinant plasmid, wherein the recombinant plasmid comprises a recombinant pET-22b(+) plasmid as an expression vector with insertion of a gene encoding a transcriptional regulation factor and a marker gene, and the nucleotide sequence of the gene encoding the transcriptional regulation factor is set forth as SEQ ID No.1.

2. The recombinant plasmid according to claim 1, further comprising a transcriptional regulation factor binding sequence set forth as SEQ ID No.5.

3. The recombinant plasmid according to claim 1, wherein the marker gene is downstream of a T7 promoter of the pET-22b(+) plasmid, replacing a nucleotide sequence of an Lac I gene on the recombinant pET-22b(+) plasmid with the nucleotide sequence of the gene encoding the transcriptional regulation factor and replacing a nucleotide sequence of an Lac O gene with the transcriptional regulation factor binding sequence.

4. The recombinant plasmid according to claim 1, wherein the marker gene is a gene encoding a fluorescent protein.

5. The recombinant plasmid according to claim 4, wherein a nucleotide sequence of the gene encoding the fluorescent protein is set forth as SEQ ID No.2.

6. Recombinant *Escherichia coli*, comprising the recombinant plasmid according to claim 1.

7. The recombinant *Escherichia coli* according to claim 6, wherein the recombinant *Escherichia coli* uses *Escherichia coli* BL21 (DE3) as an expression host.

8. A method for screening an erythritol-producing strain, comprising: inoculating the recombinant *Escherichia coli* according to claim 6 into a fermentation supernatant of strains to be screened for culture to obtain a culture solution; and confirming an erythritol-producing capacity of the strains to be screened according to an expression amount of a marker gene in the culture solution.

9. The method for screening the erythritol-producing strain according to claim 8, wherein the culture medium is a glucose-containing culture medium.

10. The method for screening the erythritol-producing strain according to claim 9, wherein a concentration of glucose in the culture medium is 10-300 g/L.

* * * * *